US012806406B2

(12) United States Patent
Stotz

(10) Patent No.: US 12,806,406 B2
(45) Date of Patent: Nov. 24, 2026

(54) PUMP FOR DELIVERING A FLUID AND METHOD OF MANUFACTURING A PUMP

(71) Applicant: Kardion GmbH, Stuttgart (DE)

(72) Inventor: Ingo Stotz, Ditzingen (DE)

(73) Assignee: Kardion GmbH, Stuttgart (DE)

( * ) Notice: Subject to any disclaimer, the term of this patent is extended or adjusted under 35 U.S.C. 154(b) by 0 days.

(21) Appl. No.: 19/323,704

(22) Filed: Sep. 9, 2025

(65) Prior Publication Data

US 2026/0007874 A1 Jan. 8, 2026

Related U.S. Application Data

(63) Continuation of application No. 18/591,825, filed on Feb. 29, 2024, now Pat. No. 12,478,776, which is a (Continued)

(30) Foreign Application Priority Data

Jan. 31, 2020 (DE) ........................ 102020102474.6

(51) Int. Cl.
*A61M 60/827* (2021.01)
*A61M 60/13* (2021.01)
(Continued)

(52) U.S. Cl.
CPC .......... *A61M 60/827* (2021.01); *A61M 60/13* (2021.01); *A61M 60/139* (2021.01);
(Continued)

(58) Field of Classification Search
CPC .. A61M 60/827; A61M 60/13; A61M 60/139; A61M 60/216; A61M 60/221;
(Continued)

(56) References Cited

U.S. PATENT DOCUMENTS

| | | | | |
|---|---|---|---|---|
| 4,682,981 A | | 7/1987 | Suzuki | |
| 5,017,103 A | * | 5/1991 | Dahl | A61M 60/419 417/420 |

(Continued)

FOREIGN PATENT DOCUMENTS

| | | |
|---|---|---|
| AU | 7993698 | 2/1999 |
| AU | 2002308409 | 12/2005 |

(Continued)

OTHER PUBLICATIONS

"ABMD—Taking a Closer Look at Impella ECP as the Pivotal Trial Gets Underway", Guggenheim, Press Release, Mar. 29, 2022, pp. 4.

(Continued)

*Primary Examiner* — Andrew J Marien
(74) *Attorney, Agent, or Firm* — Knobbe, Martens, Olson & Bear, LLP

(57) ABSTRACT

The approach presented here concerns a pump for delivering a fluid. The pump comprises an impeller, a drive device with a shaft, a shaft housing and a sealing device. The impeller is shaped to deliver the fluid. The drive device with the shaft is designed to drive the impeller. The shaft housing is shaped to receive the shaft and/or the drive device. The sealing device comprises at least one casing sealing element and/or an impeller sealing element which is received between the drive device and the impeller and which is designed to prevent fluid from entering the drive device and/or the shaft casing during operation of the pump.

14 Claims, 3 Drawing Sheets

Related U.S. Application Data continuation of application No. 17/161,326, filed on Jan. 28, 2021, now Pat. No. 11,944,805.

(51) Int. Cl.

| | |
|---|---|
| ***A61M 60/139*** | (2021.01) |
| ***A61M 60/216*** | (2021.01) |
| ***A61M 60/221*** | (2021.01) |
| ***A61M 60/408*** | (2021.01) |
| ***A61M 60/416*** | (2021.01) |
| ***A61M 60/81*** | (2021.01) |
| ***A61M 60/825*** | (2021.01) |
| ***A61M 60/861*** | (2021.01) |
| ***F04D 7/00*** | (2006.01) |
| ***F04D 29/043*** | (2006.01) |
| ***F04D 29/10*** | (2006.01) |
| ***F04D 29/18*** | (2006.01) |
| ***F04D 29/40*** | (2006.01) |
| ***F04D 29/60*** | (2006.01) |

(52) U.S. Cl.

CPC ........ *A61M 60/216* (2021.01); *A61M 60/221* (2021.01); *A61M 60/408* (2021.01); *A61M 60/416* (2021.01); *A61M 60/81* (2021.01); *A61M 60/825* (2021.01); *A61M 60/861* (2021.01); *F04D 7/00* (2013.01); *F04D 29/043* (2013.01); *F04D 29/106* (2013.01); *F04D 29/18* (2013.01); *F04D 29/406* (2013.01); *F04D 29/605* (2013.01); *A61M 2207/00* (2013.01)

(58) Field of Classification Search

CPC .. A61M 60/408; A61M 60/416; A61M 60/81; A61M 60/825; A61M 60/861; A61M 2207/00; F04D 7/00; F04D 29/043; F04D 29/106; F04D 29/18; F04D 29/406; F04D 29/605; F04D 29/126; F04D 29/628

See application file for complete search history.

(56) References Cited

U.S. PATENT DOCUMENTS

| | | | | |
|---|---|---|---|---|
| 5,290,227 | A | 3/1994 | Pasque | |
| 5,309,055 | A | 5/1994 | Leupold | |
| 5,964,694 | A * | 10/1999 | Siess | A61M 60/88 623/3.1 |
| 6,161,838 | A * | 12/2000 | Balsells | F16J 15/3212 277/572 |
| 6,794,789 | B2 * | 9/2004 | Siess | A61M 60/422 310/40 MM |
| 7,436,145 | B2 | 10/2008 | Gauthier et al. | |
| 9,474,840 | B2 | 10/2016 | Siess | |
| 10,639,460 | B2 | 5/2020 | Nitzan et al. | |
| 10,653,871 | B2 | 5/2020 | Nitzan et al. | |
| 10,780,208 | B2 | 9/2020 | Siess et al. | |
| 10,808,704 | B2 | 10/2020 | Siess et al. | |
| 10,857,274 | B2 | 12/2020 | Alexander et al. | |
| 10,926,069 | B2 | 2/2021 | Nitzan et al. | |
| 11,116,959 | B2 | 9/2021 | Alexander et al. | |
| 11,524,153 | B2 | 12/2022 | Alexander et al. | |
| 11,585,346 | B2 | 2/2023 | Bareis et al. | |
| 11,679,250 | B2 | 6/2023 | Alexander et al. | |
| 11,781,550 | B2 | 10/2023 | Siess et al. | |
| 11,813,445 | B2 | 11/2023 | Alexander et al. | |
| 11,957,892 | B2 | 4/2024 | Siess et al. | |
| 12,053,624 | B2 | 8/2024 | Alexander et al. | |
| 12,076,550 | B2 | 9/2024 | Edwards et al. | |
| 12,078,192 | B2 | 9/2024 | Gross-Hardt et al. | |
| 12,090,310 | B2 | 9/2024 | Alexander et al. | |
| 12,104,600 | B2 | 10/2024 | Mohl | |
| 12,117,007 | B1 | 10/2024 | Mohl | |
| 12,133,976 | B2 | 11/2024 | Malone et al. | |
| 12,138,438 | B2 | 11/2024 | Alexander et al. | |
| 12,151,092 | B2 | 11/2024 | Alexander et al. | |
| 12,161,857 | B2 | 12/2024 | Saul et al. | |
| 12,171,993 | B2 | 12/2024 | Higgins et al. | |
| 12,194,287 | B2 | 1/2025 | Kassel et al. | |
| 12,196,210 | B2 | 1/2025 | Siess et al. | |
| 12,201,823 | B2 | 1/2025 | Baumbach et al. | |
| 12,207,906 | B2 | 1/2025 | Tuval et al. | |
| 12,213,771 | B2 | 2/2025 | Curran et al. | |
| 12,233,251 | B2 | 2/2025 | Siess et al. | |
| 12,241,480 | B2 | 3/2025 | Corbett et al. | |
| 12,263,330 | B2 | 4/2025 | D'Ambrosio et al. | |
| 12,263,333 | B2 | 4/2025 | Stotz et al. | |
| 12,263,334 | B2 | 4/2025 | Corbett et al. | |
| 12,268,861 | B2 | 4/2025 | D'Ambrosio et al. | |
| 12,290,673 | B2 | 5/2025 | Jahangir | |
| 12,290,676 | B2 | 5/2025 | Farago et al. | |
| 12,303,678 | B2 | 5/2025 | Kerkhoffs et al. | |
| 12,303,680 | B2 | 5/2025 | Siess et al. | |
| 12,318,551 | B2 | 6/2025 | Jahangir | |
| 12,329,958 | B2 | 6/2025 | Siess et al. | |
| 12,337,163 | B2 | 6/2025 | Radman | |
| 12,343,516 | B2 | 7/2025 | Cook | |
| 12,343,518 | B2 | 7/2025 | Tuval et al. | |
| 12,343,519 | B2 | 7/2025 | Siess et al. | |
| 12,364,799 | B2 | 7/2025 | Siess et al. | |
| 12,364,850 | B2 | 7/2025 | Siess et al. | |
| 12,364,854 | B2 | 7/2025 | Wang | |
| 12,383,704 | B2 | 8/2025 | Ship et al. | |
| 12,383,724 | B2 | 8/2025 | Kirchoff et al. | |
| 12,383,727 | B2 | 8/2025 | Kassel et al. | |
| 12,390,633 | B2 | 8/2025 | Stotz et al. | |
| 12,397,146 | B2 | 8/2025 | Hart et al. | |
| D1,092,716 | S | 9/2025 | Bernazani | |
| 12,409,311 | B2 | 9/2025 | Jahangir et al. | |
| 12,415,056 | B2 | 9/2025 | Siess et al. | |
| 12,420,076 | B2 | 9/2025 | Spanier et al. | |
| 12,420,079 | B2 | 9/2025 | Das et al. | |
| 12,434,060 | B2 | 10/2025 | Tan et al. | |
| 12,440,663 | B2 | 10/2025 | Tuval et al. | |
| 12,440,665 | B2 | 10/2025 | Tuval et al. | |
| 12,447,309 | B2 | 10/2025 | Siess et al. | |
| 12,447,327 | B2 | 10/2025 | Stotz | |
| 12,453,847 | B2 | 10/2025 | Scheffler et al. | |
| 12,453,848 | B2 | 10/2025 | Tuval et al. | |
| 12,453,849 | B2 | 10/2025 | VanCamp et al. | |
| D1,101,157 | S | 11/2025 | Qi et al. | |
| 12,458,792 | B2 | 11/2025 | Zarins | |
| 12,465,744 | B2 | 11/2025 | Schuelke et al. | |
| 12,465,748 | B2 | 11/2025 | Calomeni et al. | |
| 12,478,774 | B2 | 11/2025 | Muller | |
| 12,478,775 | B2 | 11/2025 | Schlebusch et al. | |
| 12,478,776 | B2 | 11/2025 | Stotz | |
| 12,480,496 | B2 | 11/2025 | Mohl | |
| 12,491,062 | B2 | 12/2025 | Schwammenthal et al. | |
| 12,494,292 | B2 | 12/2025 | El Katerji et al. | |
| 12,502,521 | B2 * | 12/2025 | Siess | A61M 60/13 |
| 12,502,522 | B1 | 12/2025 | Van Horne et al. | |
| 12,515,036 | B2 | 1/2026 | Bette et al. | |
| 12,515,038 | B2 | 1/2026 | Weber et al. | |
| 12,521,546 | B2 | 1/2026 | Siess et al. | |
| 12,523,228 | B2 | 1/2026 | Schuelke et al. | |
| 12,539,413 | B2 | 2/2026 | Salahieh et al. | |
| 12,544,537 | B2 | 2/2026 | Siess et al. | |
| 12,544,553 | B2 | 2/2026 | Kapur et al. | |
| 12,544,554 | B2 | 2/2026 | Tuval et al. | |
| 12,544,558 | B2 | 2/2026 | Siess et al. | |
| 12,544,559 | B2 | 2/2026 | Barry | |
| 12,546,320 | B2 | 2/2026 | Siess et al. | |
| 12,551,677 | B2 | 2/2026 | Korkuch et al. | |
| 12,551,687 | B2 | 2/2026 | Grauwinkel et al. | |
| 12,558,526 | B2 | 2/2026 | Siess et al. | |
| 12,558,529 | B2 | 2/2026 | Zarins et al. | |
| 12,569,666 | B2 | 3/2026 | Siess et al. | |
| 12,569,669 | B2 | 3/2026 | Tuval et al. | |
| 12,575,841 | B2 | 3/2026 | Gao et al. | |
| 12,576,262 | B2 | 3/2026 | Edwards et al. | |
| 12,580,111 | B1 | 3/2026 | Mourran et al. | |

(56) References Cited

U.S. PATENT DOCUMENTS

| | | | |
|---|---|---|---|
| 12,589,234 | B2 | 3/2026 | Varghai et al. |
| 12,589,235 | B2 | 3/2026 | Spanier |
| 12,589,237 | B2 | 3/2026 | Mitze et al. |
| 12,589,238 | B2 | 3/2026 | Vollmer et al. |
| 12,599,758 | B2 | 4/2026 | Ryan et al. |
| 12,611,534 | B2 | 4/2026 | Haddadi et al. |
| 12,629,508 | B2 | 5/2026 | Tuval et al. |
| 12,629,509 | B2 | 5/2026 | Schwammenthal et al. |
| 12,653,999 | B2 | 6/2026 | Gentile et al. |
| 2002/0031436 | A1 | 3/2002 | Maeda et al. |
| 2002/0102169 | A1 | 8/2002 | Wampler |
| 2002/0153664 | A1* | 10/2002 | Schroeder ................ F16J 15/56 277/551 |
| 2003/0124007 | A1 | 7/2003 | Schima et al. |
| 2014/0128659 | A1 | 5/2014 | Heuring et al. |
| 2014/0368942 | A1 | 12/2014 | Harrell |
| 2015/0080743 | A1 | 3/2015 | Siess |
| 2015/0174307 | A1 | 6/2015 | Eckman et al. |
| 2015/0258262 | A1 | 9/2015 | Pfeffer |
| 2015/0362017 | A1 | 12/2015 | Bell |
| 2016/0101224 | A1 | 4/2016 | Akkerman |
| 2016/0126794 | A1 | 5/2016 | Gery |
| 2016/0184499 | A1 | 6/2016 | Ricci |
| 2017/0317573 | A1 | 11/2017 | Mueller et al. |
| 2018/0212500 | A1 | 7/2018 | Bendixen |
| 2018/0303991 | A1 | 10/2018 | Nüsser et al. |
| 2019/0199165 | A1 | 6/2019 | Carson |
| 2022/0249829 | A1 | 8/2022 | Edwards et al. |
| 2023/0063798 | A1 | 3/2023 | Edwards et al. |
| 2023/0079625 | A1 | 3/2023 | Theran et al. |
| 2023/0105131 | A1 | 4/2023 | Kerkhoffs et al. |
| 2023/0125439 | A1 | 4/2023 | Malone et al. |
| 2023/0128328 | A1 | 4/2023 | Malone et al. |
| 2023/0130285 | A1 | 4/2023 | Malone et al. |
| 2023/0149691 | A1 | 5/2023 | VanCamp et al. |
| 2023/0149692 | A1 | 5/2023 | Larsen et al. |
| 2023/0158289 | A1 | 5/2023 | Breidall et al. |
| 2023/0233834 | A1 | 7/2023 | Alexander et al. |
| 2023/0381492 | A1 | 11/2023 | Alexander et al. |
| 2024/0198084 | A1 | 6/2024 | Stotz |
| 2024/0335651 | A1* | 10/2024 | Mitze .................. A61M 60/226 |
| 2025/0032773 | A1 | 1/2025 | Baumbach et al. |
| 2025/0121177 | A1 | 4/2025 | West |
| 2025/0144397 | A1 | 5/2025 | Kassel et al. |
| 2025/0161660 | A1 | 5/2025 | Baumbach et al. |
| 2025/0170388 | A1 | 5/2025 | Kerkhoffs et al. |
| 2025/0339669 | A1 | 11/2025 | Stotz et al. |
| 2026/0048254 | A1 | 2/2026 | Scheffler et al. |
| 2026/0069857 | A1 | 3/2026 | Kassel et al. |
| 2026/0124441 | A1 | 5/2026 | Bette |

FOREIGN PATENT DOCUMENTS

| | | | |
|---|---|---|---|
| AU | 2012261669 | | 1/2013 |
| AU | 2013203301 | | 5/2013 |
| AU | 2013273663 | | 1/2014 |
| BR | PI0904483-3 | | 7/2011 |
| CA | 2 026 692 | | 4/1992 |
| CA | 2 026 693 | | 4/1992 |
| CA | 2 796 357 | | 10/2011 |
| CA | 2 947 984 | | 11/2022 |
| CN | 1222862 | A | 7/1999 |
| CN | 1254598 | A | 5/2000 |
| CN | 1376523 | A | 10/2002 |
| CN | 2535055 | Y | 2/2003 |
| CN | 1118304 | C | 8/2003 |
| CN | 2616217 | | 5/2004 |
| CN | 1202871 | C | 5/2005 |
| CN | 1833736 | A | 9/2006 |
| CN | 200977306 | | 11/2007 |
| CN | 101112628 | | 1/2008 |
| CN | 201150675 | | 11/2008 |
| CN | 201437016 | | 4/2010 |
| CN | 201618200 | | 11/2010 |
| CN | 201658687 | | 12/2010 |
| CN | 201710717 | | 1/2011 |
| CN | 201894758 | | 7/2011 |
| CN | 102545538 | | 7/2012 |
| CN | 202314596 | | 7/2012 |
| CN | 102743801 | | 10/2012 |
| CN | 103143072 | | 6/2013 |
| CN | 103845766 | | 6/2014 |
| CN | 103861162 | | 6/2014 |
| CN | 103915980 | | 7/2014 |
| CN | 203809157 | | 9/2014 |
| CN | 203842087 | | 9/2014 |
| CN | 104208763 | | 12/2014 |
| CN | 104208764 | | 12/2014 |
| CN | 203971004 | | 12/2014 |
| CN | 104274873 | | 1/2015 |
| CN | 204106671 | | 1/2015 |
| CN | 204219479 | | 3/2015 |
| CN | 103877630 | | 2/2016 |
| CN | 205215814 | | 5/2016 |
| CN | 103977464 | | 8/2016 |
| CN | 104162192 | | 9/2016 |
| CN | 104888293 | | 3/2017 |
| CN | 106512117 | | 3/2017 |
| CN | 104225696 | | 6/2017 |
| CN | 107019824 | | 8/2017 |
| CN | 206443963 | | 8/2017 |
| CN | 107281567 | | 10/2017 |
| CN | 104707194 | | 11/2017 |
| CN | 105498002 | | 6/2018 |
| CN | 106310410 | | 7/2018 |
| CN | 106902404 | | 8/2019 |
| CN | 209790495 | | 12/2019 |
| CN | 110665079 | | 1/2020 |
| CN | 210020563 | | 2/2020 |
| CN | 111166948 | | 5/2020 |
| CN | 111166949 | | 5/2020 |
| CN | 212308654 | | 1/2021 |
| CN | 215841206 | | 2/2022 |
| CN | 217828630 | | 11/2022 |
| CN | 218922664 | | 4/2023 |
| CN | 116077106 | | 5/2023 |
| CN | 116365757 | | 6/2023 |
| CN | 219250364 | | 6/2023 |
| CN | 116785582 | | 9/2023 |
| CN | 116531654 | | 11/2023 |
| CN | 116440404 | | 3/2024 |
| CN | 117018427 | | 3/2024 |
| CN | 117482377 | | 4/2024 |
| CN | 118320293 | | 7/2024 |
| CN | 118320294 | | 7/2024 |
| CN | 113769260 | | 9/2024 |
| CN | 118142074 | | 9/2024 |
| CN | 118681125 | | 9/2024 |
| CN | 118899971 | | 11/2024 |
| DE | 1 001 642 | | 1/1957 |
| DE | 11 65 144 | | 3/1964 |
| DE | 26 24 058 | | 12/1977 |
| DE | 3 545 214 | | 7/1986 |
| DE | 195 46 336 | | 5/1997 |
| DE | 695 01 834 | | 10/1998 |
| DE | 198 54 724 | | 5/1999 |
| DE | 198 21 307 | | 10/1999 |
| DE | 199 10 872 | | 10/1999 |
| DE | 199 56 380 | | 11/1999 |
| DE | 100 59 714 | | 5/2002 |
| DE | 101 55 011 | | 11/2005 |
| DE | 601 19 592 | | 9/2006 |
| DE | 20 2005 020 288 | | 6/2007 |
| DE | 10 2008 060 357 | | 6/2010 |
| DE | 10 2009 039 658 | | 3/2011 |
| DE | 20 2009 018 416 | | 8/2011 |
| DE | 10 2012 022 456 | | 5/2014 |
| DE | 10 2013 007 562 | | 11/2014 |
| DE | 10 2014 210 299 | | 12/2015 |
| DE | 10 2014 212 323 | | 12/2015 |
| DE | 11 2014 001 418 | | 12/2015 |
| DE | 10 2014 224 151 | | 6/2016 |
| DE | 20 2015 009 422 | | 7/2017 |

(56) References Cited

FOREIGN PATENT DOCUMENTS

| | | |
|---|---|---|
| DE | 10 2012 207 042 | 9/2017 |
| DE | 10 2016 013 334 | 4/2018 |
| DE | 10 2017 212 193 | 1/2019 |
| DE | 10 2018 207 611 | 11/2019 |
| DE | 10 2018 208 945 | 12/2019 |
| DE | 10 2018 211 327 | 1/2020 |
| DE | 10 2018 212 153 | 1/2020 |
| DE | 10 2018 213 350 | 2/2020 |
| DE | 11 2020 003 063 | 3/2022 |
| DE | 11 2020 004 148 | 6/2022 |
| EP | 0 050 814 | 5/1982 |
| EP | 0 629 412 | 12/1994 |
| EP | 0 764 448 | 3/1997 |
| EP | 0 855 515 | 7/1998 |
| EP | 0 890 179 | 1/1999 |
| EP | 0 904 630 | 3/1999 |
| EP | 1 013 294 | 6/2000 |
| EP | 1 186 873 | 3/2002 |
| EP | 1 475 880 | 11/2004 |
| EP | 1 169 072 | 5/2005 |
| EP | 1 176 999 | 7/2005 |
| EP | 1 801 420 | 6/2007 |
| EP | 2 009 233 | 12/2008 |
| EP | 2 098 746 | 9/2009 |
| EP | 2 047 872 | 9/2010 |
| EP | 2 129 410 | 9/2011 |
| EP | 2 403 109 | 1/2012 |
| EP | 2 187 807 | 6/2012 |
| EP | 2 330 724 | 8/2012 |
| EP | 3 326 567 | 10/2014 |
| EP | 1 898 971 | 3/2015 |
| EP | 2 519 273 | 8/2015 |
| EP | 2 438 936 | 10/2015 |
| EP | 2 438 937 | 10/2015 |
| EP | 2 960 515 | 12/2015 |
| EP | 2 968 718 | 1/2016 |
| EP | 1 996 252 | 5/2016 |
| EP | 2 475 415 | 6/2016 |
| EP | 2 906 265 | 7/2016 |
| EP | 3 069 739 | 9/2016 |
| EP | 3 127 562 | 2/2017 |
| EP | 2 585 129 | 3/2017 |
| EP | 2 646 068 | 3/2017 |
| EP | 3 222 301 | 9/2017 |
| EP | 3 222 302 | 9/2017 |
| EP | 3 020 426 | 12/2017 |
| EP | 3 038 669 | 1/2018 |
| EP | 3 062 730 | 1/2018 |
| EP | 3 180 050 | 2/2018 |
| EP | 3 287 154 | 2/2018 |
| EP | 1 789 129 | 6/2018 |
| EP | 2 366 412 | 8/2018 |
| EP | 3 205 359 | 8/2018 |
| EP | 3 205 360 | 8/2018 |
| EP | 3 456 367 | 3/2019 |
| EP | 3 119 451 | 6/2019 |
| EP | 3 542 835 | 9/2019 |
| EP | 3 542 836 | 9/2019 |
| EP | 3 189 862 | 2/2020 |
| EP | 3 711 785 | 9/2020 |
| EP | 3 711 786 | 9/2020 |
| EP | 3 711 787 | 9/2020 |
| EP | 3 069 738 | 12/2020 |
| EP | 3 131 597 | 12/2020 |
| EP | 3 142 722 | 12/2020 |
| EP | 3 579 894 | 12/2020 |
| EP | 3 188 769 | 1/2021 |
| EP | 3 490 122 | 1/2021 |
| EP | 2 869 866 | 2/2021 |
| EP | 3 398 626 | 2/2021 |
| EP | 3 487 549 | 2/2021 |
| EP | 3 113 806 | 3/2021 |
| EP | 3 615 103 | 3/2021 |
| EP | 2 344 218 | 4/2021 |
| EP | 3 436 104 | 4/2021 |
| EP | 3 749 383 | 4/2021 |
| EP | 3 808 404 | 4/2021 |
| EP | 3 131 615 | 6/2021 |
| EP | 3 338 825 | 6/2021 |
| EP | 3 432 944 | 6/2021 |
| EP | 3 684 439 | 7/2021 |
| EP | 2 582 414 | 8/2021 |
| EP | 3 407 930 | 8/2021 |
| EP | 3 782 665 | 8/2021 |
| EP | 3 782 666 | 8/2021 |
| EP | 3 782 668 | 8/2021 |
| EP | 3 858 397 | 8/2021 |
| EP | 3 216 467 | 9/2021 |
| EP | 3 884 968 | 9/2021 |
| EP | 3 884 969 | 9/2021 |
| EP | 3 027 241 | 10/2021 |
| EP | 3 579 904 | 11/2021 |
| EP | 2 628 493 | 12/2021 |
| EP | 3 914 330 | 12/2021 |
| EP | 3 928 825 | 12/2021 |
| EP | 3 556 409 | 1/2022 |
| EP | 3 624 868 | 1/2022 |
| EP | 3 624 867 | 3/2022 |
| EP | 3 689 389 | 3/2022 |
| EP | 3 697 464 | 3/2022 |
| EP | 3 737 436 | 3/2022 |
| EP | 3 967 270 | 3/2022 |
| EP | 3 972 661 | 3/2022 |
| EP | 2 967 630 | 4/2022 |
| EP | 3 142 721 | 4/2022 |
| EP | 3 520 834 | 4/2022 |
| EP | 3 586 887 | 4/2022 |
| EP | 3 638 336 | 4/2022 |
| EP | 3 689 388 | 4/2022 |
| EP | 3 765 110 | 4/2022 |
| EP | 3 782 667 | 4/2022 |
| EP | 3 829 673 | 4/2022 |
| EP | 3 976 129 | 4/2022 |
| EP | 3 984 589 | 4/2022 |
| EP | 3 986 528 | 4/2022 |
| EP | 3 649 926 | 5/2022 |
| EP | 3 653 113 | 5/2022 |
| EP | 3 654 006 | 5/2022 |
| EP | 3 735 280 | 5/2022 |
| EP | 3 897 814 | 5/2022 |
| EP | 3 990 047 | 5/2022 |
| EP | 3 219 339 | 6/2022 |
| EP | 3 737 310 | 7/2022 |
| EP | 3 899 994 | 8/2022 |
| EP | 4 039 320 | 8/2022 |
| EP | 3 487 550 | 9/2022 |
| EP | 3 606 575 | 9/2022 |
| EP | 3 834 876 | 9/2022 |
| EP | 3 000 492 | 10/2022 |
| EP | 3 600 477 | 10/2022 |
| EP | 3 897 768 | 10/2022 |
| EP | 3 914 310 | 10/2022 |
| EP | 3 914 311 | 10/2022 |
| EP | 3 000 493 | 11/2022 |
| EP | 3 858 422 | 11/2022 |
| EP | 3 866 876 | 11/2022 |
| EP | 3 941 546 | 11/2022 |
| EP | 2 892 583 | 1/2023 |
| EP | 3 393 542 | 1/2023 |
| EP | 3 597 231 | 1/2023 |
| EP | 3 656 292 | 1/2023 |
| EP | 3 768 345 | 1/2023 |
| EP | 2 868 332 | 2/2023 |
| EP | 3 003 420 | 2/2023 |
| EP | 3 539 585 | 2/2023 |
| EP | 3 956 010 | 2/2023 |
| EP | 4 137 193 | 2/2023 |
| EP | 3 046 594 | 3/2023 |
| EP | 3 127 563 | 3/2023 |
| EP | 3 256 186 | 3/2023 |
| EP | 3 288 609 | 3/2023 |
| EP | 3 538 173 | 3/2023 |
| EP | 3 606 576 | 3/2023 |
| EP | 3 927 390 | 3/2023 |

(56) References Cited

FOREIGN PATENT DOCUMENTS

| | | |
|---|---|---|
| EP | 3 384 940 | 4/2023 |
| EP | 3 441 616 | 4/2023 |
| EP | 3 938 005 | 4/2023 |
| EP | 3 946 511 | 4/2023 |
| EP | 3 544 649 | 6/2023 |
| EP | 3 634 528 | 6/2023 |
| EP | 3 912 673 | 7/2023 |
| EP | 4 218 897 | 8/2023 |
| EP | 4 218 898 | 8/2023 |
| EP | 4 218 899 | 8/2023 |
| EP | 3 615 102 | 10/2023 |
| EP | 4 252 825 | 10/2023 |
| EP | 4 252 826 | 10/2023 |
| EP | 4 252 828 | 10/2023 |
| EP | 4 419 042 | 8/2024 |
| EP | 4 384 259 | 9/2024 |
| EP | 4 429 750 | 9/2024 |
| EP | 3 618 885 | 11/2024 |
| EP | 4 039 289 | 12/2024 |
| EP | 4 477 250 | 12/2024 |
| EP | 4 084 856 | 1/2025 |
| EP | 4 483 939 | 1/2025 |
| EP | 4 483 940 | 1/2025 |
| EP | 4 491 213 | 1/2025 |
| EP | 3 522 947 | 2/2025 |
| EP | 4 429 754 | 2/2025 |
| EP | 3 998 102 | 3/2025 |
| EP | 4 429 751 | 3/2025 |
| EP | 4 429 752 | 3/2025 |
| EP | 4 429 753 | 3/2025 |
| EP | 4 023 282 | 4/2025 |
| EP | 3 950 043 | 5/2025 |
| EP | 3 955 986 | 5/2025 |
| EP | 3 958 921 | 5/2025 |
| EP | 4 218 900 | 5/2025 |
| EP | 4 429 755 | 5/2025 |
| EP | 2 830 675 | 6/2025 |
| EP | 3 965 845 | 6/2025 |
| EP | 4 039 319 | 6/2025 |
| EP | 3 668 558 | 7/2025 |
| EP | 3 780 041 | 7/2025 |
| EP | 4 095 872 | 7/2025 |
| EP | 3 668 559 | 8/2025 |
| EP | 3 746 149 | 8/2025 |
| EP | 3 823 687 | 8/2025 |
| EP | 3 848 088 | 8/2025 |
| EP | 4 119 184 | 9/2025 |
| EP | 4 218 556 | 9/2025 |
| EP | 4 046 678 | 10/2025 |
| EP | 4 034 192 | 12/2025 |
| EP | 4 100 106 | 12/2025 |
| EP | 4 134 123 | 1/2026 |
| EP | 4 201 467 | 1/2026 |
| EP | 4 233 989 | 1/2026 |
| EP | 3 650 076 | 3/2026 |
| EP | 3 768 346 | 3/2026 |
| EP | 4 034 184 | 3/2026 |
| EP | 4 069 347 | 3/2026 |
| EP | 4 090 412 | 4/2026 |
| EP | 4 114 504 | 4/2026 |
| EP | 3 852 833 | 5/2026 |
| EP | 4 159 268 | 5/2026 |
| EP | 4 223 356 | 5/2026 |
| EP | 4 241 829 | 5/2026 |
| EP | 4 252 827 | 5/2026 |
| EP | 4 279 119 | 5/2026 |
| FR | 1458525 | 3/1966 |
| GB | 0 648 739 | 1/1951 |
| GB | 2 213 541 | 8/1989 |
| GB | 2 345 387 | 7/2000 |
| GB | 2 451 161 | 12/2011 |
| GB | 2 504 177 | 1/2014 |
| GB | 2 545 062 | 6/2017 |
| GB | 2 545 750 | 6/2017 |
| JP | 59-119788 | 8/1984 |
| JP | S61-500059 | 1/1986 |
| JP | S62-113555 | 7/1987 |
| JP | S64-68236 | 3/1989 |
| JP | H02-055886 | 2/1990 |
| JP | H02-079738 | 3/1990 |
| JP | H04-002358 | 1/1992 |
| JP | H04-176471 | 6/1992 |
| JP | H04-108384 | 9/1992 |
| JP | H06-063125 | 3/1994 |
| JP | H08-057042 | 3/1996 |
| JP | H08-504621 | 5/1996 |
| JP | H10-052489 | 2/1998 |
| JP | 2888609 | 5/1999 |
| JP | 2889384 | 5/1999 |
| JP | H11-239617 | 9/1999 |
| JP | 2001-037728 | 2/2001 |
| JP | 2001-515375 | 9/2001 |
| JP | 2003-019197 | 1/2003 |
| JP | 2003-528697 | 9/2003 |
| JP | 2004-515278 | 5/2004 |
| JP | 2004-278375 | 10/2004 |
| JP | 2005-028137 | 2/2005 |
| JP | 2007-222644 | 9/2007 |
| JP | 2008-511414 | 4/2008 |
| JP | 2008-516654 | 5/2008 |
| JP | 2010-503495 | 2/2010 |
| JP | 2010-518907 | 6/2010 |
| JP | 2010-258181 | 11/2010 |
| JP | 2010-534080 | 11/2010 |
| JP | 2013-013216 | 1/2013 |
| JP | 2013-519497 | 5/2013 |
| JP | 2014-004303 | 1/2014 |
| JP | 2014-524274 | 9/2014 |
| JP | 2015-514529 | 5/2015 |
| JP | 2015-514531 | 5/2015 |
| JP | 2015-122448 | 7/2015 |
| JP | 2016-002466 | 1/2016 |
| JP | 2016-532500 | 10/2016 |
| JP | 6267625 | 1/2018 |
| JP | 2019-508128 | 3/2019 |
| JP | 2019-516458 | 6/2019 |
| JP | 6572056 | 9/2019 |
| JP | 2020-072985 | 5/2020 |
| JP | 2020-523090 | 8/2020 |
| JP | 2018-510708 | 3/2021 |
| JP | 2019-509141 | 2/2022 |
| KR | 10-2011-0098192 | 9/2011 |
| RO | 131676 | 2/2017 |
| RU | 2 051 695 | 1/1996 |
| TW | 374317 | 11/1999 |
| WO | WO 94/009835 | 5/1994 |
| WO | WO 97/037696 | 10/1997 |
| WO | WO 97/039785 | 10/1997 |
| WO | WO 99/049912 | 10/1999 |
| WO | WO 00/033446 | 6/2000 |
| WO | WO 02/022200 | 3/2002 |
| WO | WO 02/041935 | 5/2002 |
| WO | WO 02/070039 | 9/2002 |
| WO | WO 03/075981 | 9/2003 |
| WO | WO 03/103745 | 12/2003 |
| WO | WO 2005/020848 | 3/2005 |
| WO | WO 2005/028014 | 3/2005 |
| WO | WO 2005/037345 | 4/2005 |
| WO | WO 2007/033933 | 3/2007 |
| WO | WO 2007/105842 | 9/2007 |
| WO | WO 2008/017289 | 2/2008 |
| WO | WO 2008/081783 | 7/2008 |
| WO | WO 2009/010888 | 1/2009 |
| WO | WO 2009/046789 | 4/2009 |
| WO | WO 2009/046790 | 4/2009 |
| WO | WO 2009/073037 | 6/2009 |
| WO | WO 2010/119267 | 10/2010 |
| WO | WO 2011/003043 | 1/2011 |
| WO | WO 2011/081626 | 7/2011 |
| WO | WO 2011/160858 | 12/2011 |
| WO | WO 2012/018917 | 2/2012 |
| WO | WO 2012/047540 | 4/2012 |
| WO | WO 2012/112129 | 8/2012 |
| WO | WO 2013/037380 | 3/2013 |

(56) References Cited

FOREIGN PATENT DOCUMENTS

| | | |
|---|---|---|
| WO | WO 2013/120957 | 8/2013 |
| WO | WO 2013/167432 | 11/2013 |
| WO | WO 2013/173239 | 11/2013 |
| WO | WO 2014/042925 | 3/2014 |
| WO | WO 2015/039605 | 3/2015 |
| WO | WO 2015/063281 | 5/2015 |
| WO | WO 2015/085076 | 6/2015 |
| WO | WO 2015/109028 | 7/2015 |
| WO | WO 2015/172173 | 11/2015 |
| WO | WO 2015/175718 | 11/2015 |
| WO | WO 2016/028644 | 2/2016 |
| WO | WO 2016/137743 | 9/2016 |
| WO | WO 2016/146661 | 9/2016 |
| WO | WO 2016/146663 | 9/2016 |
| WO | WO 2017/004175 | 1/2017 |
| WO | WO 2017/015764 | 2/2017 |
| WO | WO 2017/021465 | 2/2017 |
| WO | WO 2017/053988 | 3/2017 |
| WO | WO 2017/060257 | 4/2017 |
| WO | WO 2017/112695 | 6/2017 |
| WO | WO 2017/112698 | 6/2017 |
| WO | WO 2017/147291 | 8/2017 |
| WO | WO 2017/159849 | 9/2017 |
| WO | WO 2017/162619 | 9/2017 |
| WO | WO 2017/205909 | 12/2017 |
| WO | WO 2018/039479 | 3/2018 |
| WO | WO 2018/088939 | 3/2018 |
| WO | WO 2018/109038 | 6/2018 |
| WO | WO 2018/139508 | 8/2018 |
| WO | WO 2018/146045 | 8/2018 |
| WO | WO 2018/197306 | 11/2018 |
| WO | WO 2019/034670 | 2/2019 |
| WO | WO 2019/035804 | 2/2019 |
| WO | WO 2019/038343 | 2/2019 |
| WO | WO 2019/057636 | 3/2019 |
| WO | WO 2019/078723 | 4/2019 |
| WO | WO 2019/135767 | 7/2019 |
| WO | WO 2019/137911 | 7/2019 |
| WO | WO 2019/138350 | 7/2019 |
| WO | WO 2019/145253 | 8/2019 |
| WO | WO 2019/158996 | 8/2019 |
| WO | WO 2019/161245 | 8/2019 |
| WO | WO 2019/180104 | 9/2019 |
| WO | WO 2019/180179 | 9/2019 |
| WO | WO 2019/180181 | 9/2019 |
| WO | WO 2019/191245 | 10/2019 |
| WO | WO 2018/135477 | 11/2019 |
| WO | WO 2018/135478 | 11/2019 |
| WO | WO 2019/211410 | 11/2019 |
| WO | WO 2019/219868 | 11/2019 |
| WO | WO 2019/219871 | 11/2019 |
| WO | WO 2019/219872 | 11/2019 |
| WO | WO 2019/219874 | 11/2019 |
| WO | WO 2019/219876 | 11/2019 |
| WO | WO 2019/219881 | 11/2019 |
| WO | WO 2019/219882 | 11/2019 |
| WO | WO 2019/219883 | 11/2019 |
| WO | WO 2019/219884 | 11/2019 |
| WO | WO 2019/219885 | 11/2019 |
| WO | WO 2019/229210 | 12/2019 |
| WO | WO 2019/229211 | 12/2019 |
| WO | WO 2019/229214 | 12/2019 |
| WO | WO 2019/229220 | 12/2019 |
| WO | WO 2019/229221 | 12/2019 |
| WO | WO 2019/229222 | 12/2019 |
| WO | WO 2019/229223 | 12/2019 |
| WO | WO 2019/229224 | 12/2019 |
| WO | WO 2019/234146 | 12/2019 |
| WO | WO 2019/239259 | 12/2019 |
| WO | WO 2019/241556 | 12/2019 |
| WO | WO 2019/243582 | 12/2019 |
| WO | WO 2019/243588 | 12/2019 |
| WO | WO 2020/003110 | 1/2020 |
| WO | WO 2020/011760 | 1/2020 |
| WO | WO 2020/011795 | 1/2020 |
| WO | WO 2020/011797 | 1/2020 |
| WO | WO 2020/016438 | 1/2020 |
| WO | WO 2020/028312 | 2/2020 |
| WO | WO 2020/028537 | 2/2020 |
| WO | WO 2020/030700 | 2/2020 |
| WO | WO 2020/064911 | 4/2020 |
| WO | WO 2020/073047 | 4/2020 |
| WO | WO 2020/132211 | 6/2020 |
| WO | WO 2020/187797 | 9/2020 |
| WO | WO 2020/219430 | 10/2020 |
| WO | WO 2020/234785 | 11/2020 |
| WO | WO 2020/242881 | 12/2020 |
| WO | WO 2020/245649 | 12/2020 |
| WO | WO 2020/264174 | 12/2020 |
| WO | WO 2021/046275 | 3/2021 |
| WO | WO 2021/062265 | 4/2021 |
| WO | WO 2021/067169 | 4/2021 |
| WO | WO 2021/067691 | 4/2021 |
| WO | WO 2021/119478 | 6/2021 |
| WO | WO 2021/150777 | 7/2021 |
| WO | WO 2021/152013 | 8/2021 |
| WO | WO 2021/191106 | 9/2021 |
| WO | WO 2023/040546 | 12/2021 |
| WO | WO 2022/056542 | 3/2022 |
| WO | WO 2022/063650 | 3/2022 |
| WO | WO 2022/072944 | 4/2022 |
| WO | WO 2022/076862 | 4/2022 |
| WO | WO 2022/076948 | 4/2022 |
| WO | WO 2022/109589 | 5/2022 |
| WO | WO 2022/109590 | 5/2022 |
| WO | WO 2022/109591 | 5/2022 |
| WO | WO 2022/173977 | 8/2022 |
| WO | WO 2023/226779 | 9/2022 |
| WO | WO 2023/278599 | 1/2023 |
| WO | WO 2023/014742 | 2/2023 |
| WO | WO 2023/037162 | 3/2023 |
| WO | WO 2023/049813 | 3/2023 |
| WO | WO 2024/160098 | 4/2023 |
| WO | WO 2023/076461 | 5/2023 |
| WO | WO 2023/076869 | 5/2023 |
| WO | WO 2024/104184 | 5/2024 |
| WO | WO 2025/226734 | 10/2025 |
| WO | WO 2026/072583 | 4/2026 |

OTHER PUBLICATIONS

Delgado et al., “Interventional Treatment of Advanced Ischemic Heart Disease”, Percutaneous Mechanical Assist Devices, Ch. 6, Springer, 2009, pp. 85-91.

Delgado et al., “Interventional Treatment of Advanced Ischemic Heart Disease”, The Future of Treatment of Advanced Ischemic Heart Disease, Ch. 8, Springer, 2009, pp. 129-142.

Eeckhout, Md, PhD, et al., “Handbook of Complications During Percutaneous Cardiovascular Interventions”, 2007 Informa UK Ltd., Ch. 12, pp. 167-177.

“FDA Approves Abiomed’s Heart Pump Impella, Shares Rise”, Reuters 2008 press release, Jun. 2, 2008, https://jp.reuters.com/article/us-abiomed/fda-approves-abiomeds-heart-pump-impella-shares-rise-idUSBNG131420080602/, 1 page.

Lake et al., “Pediatric Cardiac Anesthesia”, 4th Edition, 2005, Ch. 15, pp. 291-303.

Machiraju, Venkat R., “Redo Cardiac Surgery in Adults”, Practical Approaches to the Current “On-Pump” Redo Coronary Artery Bypass Surgery, Ch. 2, Springer, 2012, pp. 7-19.

Machiraju, Venkat R., “Redo Cardiac Surgery in Adults”, Options for Advanced Mechanical Support for Cardiogenic Shock Complicating Cardiac Reoperations, Ch. 9, Springer, 2012, pp. 67-80.

Machiraju, Venkat R., “Redo Cardiac Surgery in Adults”, Percutaneous Approaches to Valvular Heart Disease After Previous Cardiac Surgery, Ch. 21, Springer, 2012, pp. 195-200.

Parrillo et al., “Critical Care Medicine”, Principles of Diagnosis and Management in the Adult, Elsevier, 4th Edition, 2014, Chapters 4 & 29, pp. 47-58.e1 and 442-469.e4.

Vincent, Md, PhD, et al., “Textbook of Critical Care”, Acute Coronary Syndromes: Therapy, Elsevier, 7th Edition, Ch. 78, 2017, pp. 520-531.e3.

(56) References Cited

OTHER PUBLICATIONS

Vincent, Md, PhD, et al., "Textbook of Critical Care", Mechanical Support in Cardiogenic Shock, Elsevier, 7th Edition, Ch. 91, 2017, pp. 637-648.e3.

Vollkron et al., "Advanced Suction Detection for an Axial Flow Pump", Artificial Organs, 2006, vol. 30, No. 9, pp. 665-670.

Vollkron et al., "Development of a Suction Detection System for Axial Blood Pumps", Artificial Organs, 2004, vol. 28, No. 8, pp. 709-716.

Bourque et al., "HeartMate III: Pump Design for a Centrifugal LVAD with a Magnetically Levitated Rotor", ASA/0 Journal 2001, pp. 401-405.

New Hampshire Ball Bearings, Inc., "Engineering Reference, Rod End & Spherical Bearings", https://www.nhbb.com/index.php/knowledge-center/engineering-reference/rod-end-spherical-bearings/self-lubricating-liner-systems, 2021, pp. 13.

Nojiri et al., "Development of Terumo Implantable Left Ventricular Assist System (T-ILVAS) with a magnetically Suspended Centrifugal Pump", The Japanese Society for Artificial Organs, 1999, pp. 3-7.

Schmitz-Rode, T, Graf, J, Pfeffer, J. et al. "An Expandable Percutaneous Catheter Pump for Left Ventricular Support: Proof of Concept", JACC. Jun. 2005, 45 (11) 1856-1861.

* cited by examiner

PUMP FOR DELIVERING A FLUID AND METHOD OF MANUFACTURING A PUMP

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application is a continuation of U.S. patent application Ser. No. 18/591,825, entitled PUMP FOR DELIVERING A FLUID AND METHOD OF MANUFACTURING A PUMP, and filed Feb. 29, 2024, which is a continuation of U.S. patent application Ser. No. 17/161,326, entitled PUMP FOR DELIVERING A FLUID AND METHOD OF MANUFACTURING A PUMP, and filed Jan. 28, 2021, which claims the benefit of priority to German patent application number 102020102474.6, entitled PUMP FOR DELIVERING A FLUID AND METHOD OF MANUFACTURING A PUMP, and filed Jan. 31, 2020, the disclosure of which is hereby incorporated by reference herein in its entirety for all purposes and forms a part of this specification.

BACKGROUND

Field

This disclosure relates generally to cardiac pumps, in particular to cardiac pumps with seals.

Description of the Related Art

Cardiovascular support systems, so-called "VAD" (Ventricular Assist Device) systems, are used to provide cardiovascular support for patients with heart failure. These systems perform a partial or complete pumping function for a blood flow through the heart. These systems are divided into temporary systems for short-term cardiac support and permanent systems. The temporary systems are used, among other things, to bridge the time until a suitable donor heart is available and can be implanted. The permanent systems are used for long-term residence on or in the patient. A component of such systems is a blood pump, typically a centrifugal pump in the form of a turbopump, which is driven by an integrated electric motor and generates the required blood flow by means of an impeller. Conventional pumps have deficient seals or systems that require complex procedures, such as purging. Improvements to these and other drawbacks of existing cardiac pumps are desirable.

SUMMARY OF CERTAIN INVENTIVE ASPECTS

The embodiments disclosed herein each have several aspects no single one of which is solely responsible for the disclosure's desirable attributes. Without limiting the scope of this disclosure, its more prominent features will now be briefly discussed. After considering this discussion, and particularly after reading the section entitled "Detailed Description," one will understand how the features of the embodiments described herein provide advantages over existing systems, devices and methods for cardiac pumps.

The following disclosure describes non-limiting examples of some embodiments. For instance, other embodiments of the disclosed systems and methods may or may not include the features described herein. Moreover, disclosed advantages and benefits can apply only to certain embodiments and should not be used to limit the disclosure.

Against the above background, the approaches presented here introduce a pump for delivering a fluid and a method for manufacturing a pump, further a device using this method, and also a corresponding computer program according to the main requirements. The measures listed in the dependent claims allow for advantageous further training and improvements of the device specified in the independent claims. The subject of the present approach is also a computer program.

The advantages that can be achieved with the approaches presented are that a pump is created whose shaft housing is protected from fluid ingress by using only one or very few sealing elements.

In one aspect, a pump for transferring a fluid has an impeller, a drive device with a shaft, a shaft housing and a sealing device. The impeller is designed to pump the fluid. The drive device with the shaft is designed to drive the impeller. The shaft housing is designed to accommodate the shaft and in addition or alternatively the drive device. The sealing device has at least one housing sealing element and additionally or alternatively an impeller sealing element which is accommodated between the drive device and the impeller and which is designed to prevent the fluid from entering the shaft housing and additionally or alternatively the drive device during operation of the pump.

The impeller can have a cylindrically shaped or tapered basic body, which is rotatable around a longitudinal axis during operation of the impeller. Radially around the longitudinal axis, the basic body can have one or more blades or vanes to create a fluid flow or fluid suction when the impeller rotates in the fluid. For this purpose the vane or vanes can be arranged spirally wound around an outer wall of the basic body. A body of revolution is typically created by the rotation of one or more so-called "B-Splines". In addition to the shaft, the drive device can have a motor coupled to the shaft, for example an electric motor. The shaft can be straight. The shaft housing can be tubular to accommodate at least part or all of the shaft or the entire drive unit with the motor. The housing sealing element and additionally or alternatively the impeller sealing element can be made of a solid, for example elastic, material. Thanks to the sealing device, fluid penetration into the shaft housing and additionally or alternatively the drive device is prevented or minimized during operation of the pump. It is advantageous to dispense with additional sealing media such as barrier media or flushing media.

The housing sealing element can be attached to an inner side of the shaft housing and can be arranged additionally or alternatively around the shaft. Thus, the sealing element can be arranged to seal the shaft against an inner side of the shaft housing to prevent or minimize the penetration of the fluid into the shaft housing. For example, the housing sealing element can be shaped as a sealing ring, especially a rotary shaft seal. According to one design, the casing sealing element can be attached to an inlet opening of the shaft casing facing the impeller in order to seal this inlet opening.

The impeller sealing element can be fixed to the impeller and additionally or alternatively arranged around the shaft and additionally or alternatively contacting the shaft housing. In this way the shaft can be sealed against the shaft housing in the axial direction. For example, the impeller sealing element can be designed as another sealing ring, in particular an axial shaft seal. The axial shaft seal can also be described as a "V-ring" and has a v-shaped or plate-shaped flexible sealing lip that extends away from an annular base body of the axial shaft seal. The sealing lip can be attached to the impeller.

The impeller sealing element can be preloaded towards the shaft in mounted condition. A preload can be achieved by a deformation of the impeller sealing element, for example, if the impeller sealing element has the previously described deformation of the axial shaft seal. However, the preload can also be effected by means of an additional spring element.

It is also advantageous if the impeller sealing element has, according to a design, at least one gap sealing element arranged to fluidically seal a gap between the shaft housing and the impeller to prevent the fluid from entering the gap. The gap sealing element can be an additional sealing ring. An outside diameter of the gap sealing element may be larger than an outside diameter of the impeller sealing element. A sealing effect in axial direction can be increased by an additional gap sealing element.

A free end of the shaft can be supported in the impeller. This creates a stable mechanical coupling between the shaft and the impeller. Alternatively, the free end of the shaft and the impeller can be connected contactlessly by means of a magnetic coupling.

According to one design, the pump can have a bearing device for radial, and additionally or alternatively, axial bearing of the shaft in the shaft housing. This bearing arrangement can be used to ensure stability of the shaft during operation of the pump.

A method for manufacturing a pump for delivering a fluid is also presented. The process includes a step of providing and a step of assembling. In the step of providing, an impeller for conveying the fluid, a drive means with a shaft designed to drive the impeller, a shaft housing for receiving the shaft and additionally or alternatively the drive means and a sealing means with at least one housing sealing element and additionally or alternatively, an impeller sealing element are provided as components. In the step of assembling the components are assembled to produce the pump, whereby in the step of assembling the housing sealing element and additionally or alternatively the impeller sealing element is accommodated between the drive device and the impeller in order to prevent or reduce fluid penetration into the shaft housing and additionally or alternatively the drive device during operation of the pump.

This procedure can be implemented in software or hardware, for example, or in a mixture of software and hardware in an ECU, for example.

The approach presented here also creates a device that is designed to perform, control, or implement the steps of a variant of a process presented here in appropriate facilities. Also, by this design variant of the approach in form of a device the task underlying the approach can be solved fast and efficiently.

For this purpose, the device can have at least one computing unit for processing signals or data, at least one memory unit for storing signals or data, at least one interface to a sensor or an actuator for reading in sensor signals from the sensor or for outputting data or control signals to the actuator and/or at least one communication interface for reading in or outputting data embedded in a communication protocol. The computing unit may be, for example, a signal processor, a microcontroller or the like, whereby the memory unit may be a flash memory, an EEPROM or a magnetic memory unit. The communication interface may be designed to read or output data wirelessly and/or wired, whereby a communication interface that can read or output wired data can, for example, read or output this data electrically or optically from a corresponding data transmission line or output it to a corresponding data transmission line.

A device can be understood as an electrical device that processes sensor signals and outputs control and/or data signals depending on them. The device can have an interface, which can be hardware and/or software based. In the case of a hardware-based design, the interfaces can be part of a so-called system ASIC, which contains various functions of the device. However, it is also possible that the interfaces are own integrated circuits or at least partly consist of discrete components. In the case of a software-based education, the interfaces can be software modules, which for example are available on a microcontroller next to other software modules.

A computer program product or computer program with program code, which may be stored on a machine-readable carrier or storage medium, such as a semiconductor memory, a hard disk memory or an optical memory, and which is used to carry out, implement and/or control the steps of the process according to one of the forms of execution described above, is also advantageous, in particular if the program product or program is executed on a computer or device.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the drawing, can be arranged, substituted, combined, and designed in a wide variety of different configurations, all of which are explicitly contemplated and make part of this disclosure.

Execution examples of the approaches presented here are shown in the drawings and explained in more detail in the following description. It shows.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION OF CERTAIN EMBODIMENTS

The following detailed description is directed to certain specific embodiments of the development. In this description, reference is made to the drawings wherein like parts or steps may be designated with like numerals throughout for clarity. Reference in this specification to "one embodiment," "an embodiment," or "in some embodiments" means that a particular feature, structure, or characteristic described in connection with the embodiment is included in at least one embodiment of the invention. Moreover, various features are described which may be exhibited by some embodiments and not by others. Similarly, various requirements are described which may be requirements for some embodiments but may not be requirements for other embodiments. Reference will now be made in detail to embodiments of the invention, examples of which are illustrated in the accompanying drawings. Wherever possible, the same reference numbers will be used throughout the drawings to refer to the same or like parts.

In the following description of favorable execution examples of the present approach, the same or similar reference signs are used for the elements represented in the different figures and which have a similar effect, whereby a repeated description of these elements is omitted.

Figure 1:
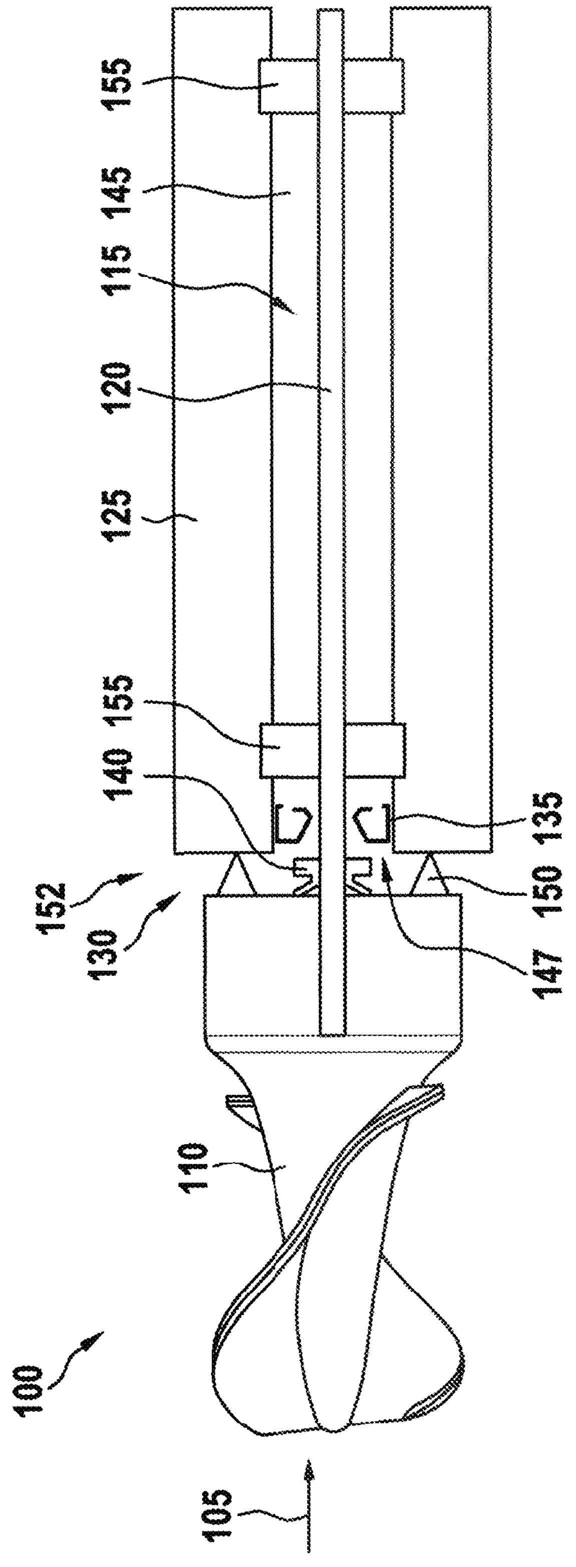
FIG. 1 is a schematic side view of a pump for pumping a fluid according to a design example.

FIG. 1 shows a schematic side view of a pump 100 for pumping a fluid 105 according to a design example. The pump 100 is designed and shaped for use in a fluid channel such as a blood vessel.

The pump 100 has an impeller 110, a drive device 115 with a shaft 120, a shaft housing 125 and a sealing device 130. The impeller 110 is designed to pump the fluid 105. The drive device 115 with shaft 120 is designed to drive the impeller 110. The shaft housing 125 is designed to accommodate the shaft 120 and/or the drive device 115 and is also referred to as the "housing" in the following. The sealing device 130 comprises at least one casing sealing element 135 and/or one impeller sealing element 140, which is accommodated between the drive device 115 and the impeller 110 and which is designed to prevent fluid 105 from entering the drive device 115 and/or the shaft casing 125 during operation of the pump 100.

According to this design example, the impeller 110 only has an exemplary tapered basic body, which can be rotated around a longitudinal axis during operation of the impeller 110. Radially around the longitudinal axis, the basic body according to this design example has two blades in order to generate a fluid flow or fluid suction in the fluid 105 when the impeller 110 rotates. For this purpose, the blades are arranged spirally wound around an outer wall of the basic body according to this design example. A body of rotation of the impeller 110 is created by the rotation of one or more so-called "B-spindles". According to an alternative design example, the impeller 110 has a differently shaped, for example cylindrical, basic body and/or a different number of blades or vanes. According to this design example, the drive unit 115, which will also be referred to as "drive" in the following, has a motor 145, for example in the form of an electric motor. According to this design example, the motor 145 is coupled to the shaft 120. The shaft 120 is straight according to this design example. The shaft housing 125 is correspondingly tubular according to this design example and accommodates at least the shaft 120 or, according to this design example, the entire drive unit 115 with the motor 145 completely. According to an alternative design example, the motor 145 is arranged outside the shaft housing 125. According to this design example, the housing sealing element 135 and/or impeller sealing element 140 is made of a strong but elastic material. In other words, the casing sealing element 135 and/or impeller sealing element 140 has no liquid or semi-liquid material.

According to this design example, the housing sealing element 135 is attached to an inner side of the shaft housing 125 and/or arranged around the shaft 120. According to this design example, the housing sealing element 135 is formed as a sealing ring, according to this design example as a rotary shaft seal. According to this design example, the casing sealing element 135 is attached to an inlet opening 147 of the shaft casing 125 facing the impeller 110. According to one design example, the casing sealing element 135 is fixed directly to the inlet opening 147.

The additional or alternative impeller sealing element 140 is attached to the impeller 110 and/or arranged around the shaft 120 and/or the shaft casing 125 in contact according to this design example. According to this design example, the impeller sealing element 140 is designed as an additional sealing ring, here an axial shaft seal. The axial shaft seal can also be described as a "V-ring". According to this design example, this V-ring has a V-shaped or plate-shaped flexible sealing lip that extends away from an annular base body of the axial shaft seal. According to this design example, the sealing lip is attached to the impeller 110.

The impeller sealing element 140 is also preloaded towards the shaft 120 in the mounted state according to this design example. A pretension is caused by a deformation of the impeller sealing element 140. According to an alternative design example, the pump 100 has a spring element which causes the preload.

Furthermore, according to this design example, the impeller sealing element 140 has at least one gap sealing element 150, which is arranged to fluidically seal a gap 152 between the shaft housing 125 and the impeller 110 in order to prevent the fluid 105 from entering the gap 152. According to this design example, the gap sealing element 150 is designed as an additional sealing ring. According to this design example, an outer diameter of the gap sealing element 150 is larger than an outer diameter of the impeller sealing element 140. According to this design example, the impeller sealing element 140 is arranged coaxially with respect to the additional sealing ring in a passage opening of the additional sealing ring.

A free end of the shaft 120 is fixed in the impeller 110 according to this design example. According to an alternative design example, the free end of the shaft 120 and the impeller 110 are connected without contact by means of a magnetic coupling, whereby a driving force of the motor 145 is magnetically transferable to the impeller 110.

The pump 100 also has, according to this design example, a bearing device 155 for radial and/or axial bearing of the shaft 120 in the shaft housing 125. For this purpose, the bearing device 155 according to this design example has two bearing elements at two opposite ends of an interior of the shaft housing 125, in which the shaft 120 is, for example, centrally mounted. According to this design example, the housing sealing element 135 is arranged outside a space bounded by the two bearing elements.

The pump 100 presented here can be used and shaped as a blood pump for a cardiac support system. According to one design example, the Pump 100 is designed as a VAD pump for short-term implantation with a contacting radial and/or axial seal.

For temporary/short-time used VAD-Pumps 100 it is important that they can be implanted very quickly. According to this design example, a system as simple as possible is used for this purpose. One of the tasks of the present approach is to use only one or more sealing elements 135, 140, 150 and to dispense with liquid or partially liquid media such as flushing media or barrier media or an external forced flushing for sealing.

According to this design example, the pump 100 presented here has the electric drive in the form of the electric motor 145, the rotating shaft 120, the impeller 110, the bearing device 155, the shaft housing 125 and at least one sealing element 135, 140, 150, which is firmly connected to the housing 125 according to a design example in the form of the housing sealing element 135 and has a sealing function with respect to the rotating shaft 120 and/or the impeller 110. Additionally or alternatively, the pump 100 has a sealing element in the form of the impeller sealing element 140 and/or gap sealing element 150, which seals the housing 125 against the rotating impeller 110 in the axial direction. According to this design example, the impeller 110 consists of a core with, for example, a hub and at least two or more blades. During operation of the pump 100, the fluid 105 is fed axially to the impeller 110 (suction) and discharged radially/diagonally through openings in an impeller housing of the impeller 110 not shown here. According to this design example, the impeller 110 is firmly connected to the drive shaft 120 of the motor 145, which provides the required drive power. According to this design example, the shaft 120 is supported by at least one radial and/or at least one axial bearing. Optionally, the bearings are also realized in combination with a radial-axial bearing. According to one possible design example, the housing 125 has at least one sealing element 135 to the impeller 110. According to another design example, this at least one sealing element 140, 150 is attached to the impeller 110. The seal is of contact design, i.e. according to one design example, the sealing element 135, 140 is always in contact with the shaft 120 and the casing 125. Furthermore, at least one (further) sealing element 140, which seals the shaft 120 against the casing 125, is arranged optionally/alternatively. This is designed according to a design example in such a way that the sealing element 140 is preloaded towards the shaft 120. According to one design example, this is realized with a spring or according to another design example, it is ensured by shaping the elastic sealing element 140. One possible design of the housing sealing element 135 is a rotary shaft seal. The axial shaft sealing ring is a possible design of the alternative/optional sealing element 140.

According to one design example, the VAD Pump 100 has a maximum outside diameter of less than five millimeters, in another design example it has an outside diameter of less than eight millimeters. According to one design example, the Pump 100 is designed for a short-term use of less than 24 hours, in another design example for a use of less than ten days, in another design example for less than 28 days and in another design example for less than or equal to six months.

Figure 2:
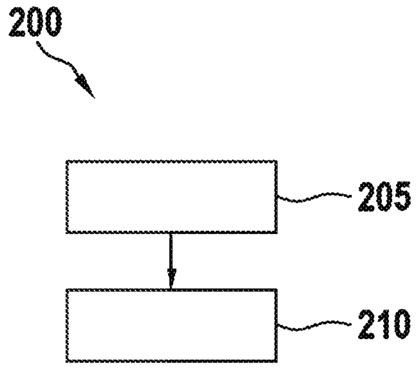
FIG. 2 is a flow chart of a process for manufacturing a pump for pumping a fluid according to a design example.

FIG. 2 shows a flowchart of a process 200 for manufacturing a pump for pumping a fluid according to a design example. This can be the pump described in FIG. 1.

Procedure 200 includes a 205 step of provisioning and a 210 step of assembly. In step 205 of providing, an impeller for conveying the fluid, a drive means with a shaft adapted to drive the impeller, a shaft housing for receiving the shaft and/or the drive means, and a sealing means with at least one housing sealing element and/or one impeller sealing element are provided. In the step 210 of assembling, the components are assembled to produce the pump, wherein in the step of assembling, the housing sealing element and/or the impeller sealing element is received between the drive means and the impeller to prevent fluid from entering the shaft housing and/or the drive means during operation of the pump.

According to a design example, in step 210 of the assembly process, the impeller is also connected to the shaft and/or the shaft and/or drive unit is mounted in the shaft housing in any order.

Figure 3:
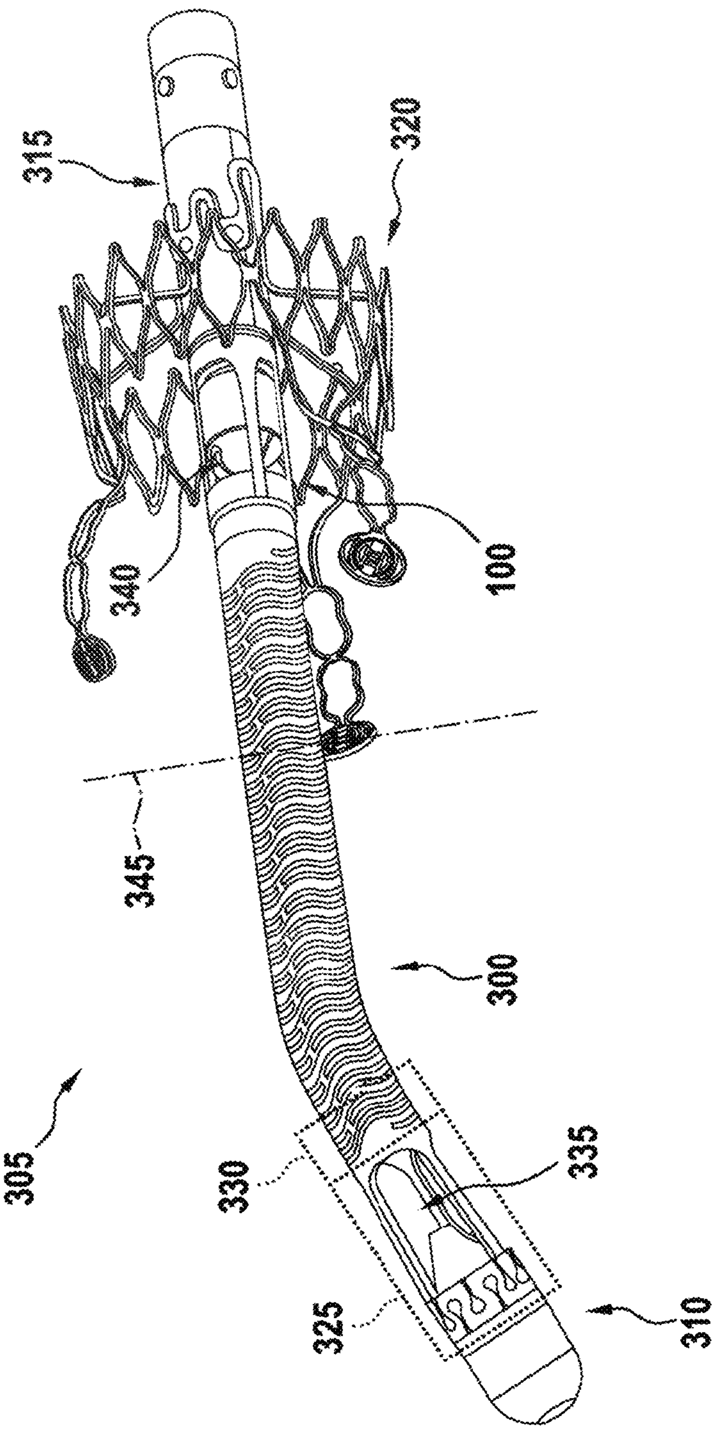
FIG. 3 is a perspective side view of a pump according to a design example.

FIG. 3 shows a perspective side view of a pump 100 according to an execution example. This can be an example of the pump 100 described in FIG. 1 or 2.

According to this design example, the pump 100 also has an inlet line 300 and is implemented as a cardiac support system 305, which is designed as a left ventricular assist device (LVAD) for positioning across an aortic valve. The elongated axial design of the Cardiac Support System 305 shown here with a substantially constant outer diameter allows transfemoral or transaortic implantation of the Cardiac Support System 305 for easy placement by means of a catheter in a blood vessel, such as the aorta. The inflow line 300 has an exemplary inclination of the longitudinal axis according to the shape for the aortic valve position and thus a slightly curved shape. The Cardiac Support System 305 comprises the inflow line 300, the pump 100, a head unit 310, a housing section 315 and an anchoring frame 320. The inlet line 300, which can also be called the "suction trunk", is located between the head unit 310 and the pump 100. The pump 100 is housed in the housing section 315, to which an optional anchoring frame 320 can be attached.

The inlet line 300 is designed according to a design example to direct a fluid flow to the pump 100 of the Cardiac Support System 305. According to this design example, the inlet line 300 comprises an inlet head section 325 and a contour section 330. The inlet head section 325 has at least one inlet opening 335 for introducing the fluid flow into the inlet line 300. The contour section 330 has an inner surface contour. The contour section 330 is arranged adjacent to the inlet head section 325. An inner diameter of contour section 330 is larger at a first position than the inner diameter at a second position. The inner surface contour has a fillet at the second position to reduce the inner diameter.

In the design example shown here, the feed head section 325 and the contour section 330 are marked as examples. Especially the contour section 330 optionally comprises a smaller or larger part of the feed line 300 than shown here. In the implanted state of the Cardiac Support System 305, the supply head section 325 and the contour section 330 are located in the left heart chamber. A further section of the supply line 300 is led through the aortic valve, and a section of the Cardiac Support System 305 with the pump 100 is located in a section of the aorta. A pump outlet 340 in the area of the pump 100 directs the fluid flow delivered through the inlet line 300 into the aorta. A marking 345 shows an example of a position of a heart valve, e.g. the aortic valve, through which the supply line 300 is passed in order to position the Cardiac Support System 305.

At least one inlet edge of the inlet opening 335 of the inlet head section 325 is rounded according to the design example shown here. In this example, the inlet opening 335 is designed as a window-shaped inlet cut into the inlet head section 325.

According to the design example shown here, a length of the contour section 330 corresponds to a radius of the feed line 300 within a tolerance range. The tolerance range means a maximum deviation of twenty percent from the radius of the feed line 300.

A cardiac support system limited in terms of installation space, such as the cardiac support system 305 shown here as an example, which can be implanted minimally invasively, has a comparatively low power consumption for a given pump efficiency. The efficiency is limited by the friction in the pump 100. The pressure loss or friction in the feed line 300 when conducting the fluid flow from the inlet port 335 of the feed head section 325 in the heart chamber to the pump 100 is adjustable by the shaping of the feed line 300. For this purpose, the inlet edges of the inlet opening 335 are rounded to reduce the pressure loss. This is the only way to prevent flow separation. The flow separation is suppressed by an inlet inner surface contour in the form of the contour section 330 formed according to the approach presented here, thus reducing the pressure loss.

If an execution example includes an "and/or" link between a first feature and a second feature, this should be read in such a way that the execution example has both the first feature and the second feature according to one execution form and either only the first feature or only the second feature according to another execution form.

Various modifications to the implementations described in this disclosure will be readily apparent to those skilled in the art, and the generic principles defined herein can be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations, unless otherwise stated.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

What is claimed is:

1. A cardiac pump for delivering a fluid, the cardiac pump comprising:

an impeller configured to convey the fluid;

a shaft configured to drive the impeller;

a shaft housing configured to receive the shaft; and at least one housing sealing element disposed between the shaft and the shaft housing and configured to prevent the fluid from penetrating the shaft housing during operation of the cardiac pump, wherein the at least one housing sealing element comprises:

a first wall extending from a second wall to a third wall;

the second wall adjacent to the shaft; and the third wall adjacent to the shaft housing, wherein the second wall and the third wall extend from the first wall in a direction away from the impeller.

2. The cardiac pump according to claim 1, further comprising a spring configured to pre-load the at least one housing sealing element toward the shaft.

3. The cardiac pump according to claim 1, wherein the at least one housing sealing element is C-shaped.

4. The cardiac pump according to claim 1, wherein the at least one housing sealing element is fixed to an inner side of the shaft housing or is arranged around the shaft.

5. The cardiac pump according to claim 1, wherein the at least one housing sealing element comprises a sealing ring.

6. The cardiac pump according to claim 1, further comprising a plurality of bearings between the shaft and the shaft housing, the plurality of bearings configured to support the shaft.

7. The cardiac pump according to claim 6, further comprising an at least one second sealing element distal to at least one bearing of the plurality of bearings.

8. The cardiac pump according to claim 1, wherein the at least one housing sealing element comprises a liquid or partially liquid medium.

9. The cardiac pump according to claim 1, wherein the shaft is straight.

10. The cardiac pump according to claim 1, wherein the shaft housing is tubular.

11. The cardiac pump according to claim 1, wherein the shaft housing is configured to receive a motor of a drive.

12. The cardiac pump according to claim 1, wherein the at least one housing sealing element comprises a rotary shaft seal.

13. The cardiac pump according to claim 1, wherein the at least one housing sealing element is made of an elastic material.

14. The cardiac pump according to claim 1, wherein the at least one housing sealing element is in contact with the shaft and the shaft housing.

* * * * *